(12) United States Patent
Ackley et al.

(10) Patent No.: US 9,863,910 B1
(45) Date of Patent: Jan. 9, 2018

(54) TFT-BASED SENSOR WITH MULTIPLE SENSING MODALITIES

(71) Applicants: Donald E. Ackley, Cardiff, CA (US); Chan-Long Shieh, Paradise Valley, AZ (US)

(72) Inventors: Donald E. Ackley, Cardiff, CA (US); Chan-Long Shieh, Paradise Valley, AZ (US)

(73) Assignee: CBRITE INC., Goleta, CA (US)

( * ) Notice: Subject to any disclaimer, the term of this patent is extended or adjusted under 35 U.S.C. 154(b) by 0 days.

(21) Appl. No.: 15/261,627

(22) Filed: Sep. 9, 2016

(51) Int. Cl.
*G01N 27/414* (2006.01)
*C12Q 1/68* (2006.01)
*C12M 1/34* (2006.01)
*B81B 3/00* (2006.01)

(52) U.S. Cl.
CPC ....... *G01N 27/4145* (2013.01); *B81B 3/0089* (2013.01); *C12M 1/3446* (2013.01); *C12M 1/3476* (2013.01); *C12Q 1/6825* (2013.01); *G01N 27/414* (2013.01); *B81B 2201/0214* (2013.01)

(58) Field of Classification Search
CPC ............. G01N 27/414; G01N 27/4145; C12Q 1/6825; B81B 2201/0214; B81B 3/0064; B81B 3/0089; C12M 1/3446; C12M 1/3476
See application file for complete search history.

(56) References Cited

U.S. PATENT DOCUMENTS

| 6,653,083 | B2 * | 11/2003 | Emoto | C12Q 1/6825 |
| | | | | 435/287.2 |
| 7,214,346 | B2 * | 5/2007 | Harper | G01N 21/07 |
| | | | | 422/504 |
| 8,994,946 | B2 * | 3/2015 | McCaffrey | C12Q 1/6869 |
| | | | | 356/318 |
| 2008/0318243 | A1 * | 12/2008 | Haga | C12Q 1/6825 |
| | | | | 435/5 |
| 2009/0278556 | A1 * | 11/2009 | Man | G01N 27/4146 |
| | | | | 324/693 |

OTHER PUBLICATIONS

Nakazato ("An Integrated ISFET Sensor Array", Sensors, 9, pp. 8831-8851, 2009).*
Terasaki et al. ("Photosensor Based on an FET Utilizing a Biocomponent of Photosystem I for Use in Imaging Devices", Langmuir, 25(19), pp. 11969-11974, 2009).*

* cited by examiner

*Primary Examiner* — Yasser A Abdelaziez
(74) *Attorney, Agent, or Firm* — Parsons & Goltry; Robert A. Parsons; Michael W. Goltry (57) ABSTRACT

A metal oxide TFT-based sensor with multiple sensing modalities including an ion sensitive detector having an extended gate, a reservoir constructed to receive a sample carrying solution, and an ion sensitive electrode. The sensor further including a photodiode, a plurality of metal-oxide thin film transistors and a signal output. A pair of the metal-oxide thin film transistors are coupled to the photodiode, the ion sensitive detector and the output so as to provide output signals at the output alternately representative of ion emissions sensed by the ion sensitive detector and fluorescence events sensed by the photodiode.

24 Claims, 5 Drawing Sheets

TFT-BASED SENSOR WITH MULTIPLE SENSING MODALITIES

FIELD OF THE INVENTION

This invention generally relates to one-chip multimodal sensors and more specifically to a modular platform for different biological functions or more specifically to a lab-on-a-chip for complete analysis.

BACKGROUND OF THE INVENTION

One-chip multimodal sensors that can perform a variety of different biological functions are highly sought after and extremely valuable in the medical industry. Such sensors can provide a modular platform for: liquid biopsy including cell enrichment and cell characterization, such as electrical, optical and fluorescence; and sequencing of genomes including optical detection, charge detection and dual detection.

To carry out the sequencing of the human genome, the DNA (deoxyribonucleic acid) is cut into short fragments, the fragments are sequenced simultaneously and the data may then be assembled using sophisticated computer technology. DNA sequencing is the process of determining the precise order of nucleotides (thymine, adenine, guanine, and cytosine) within a DNA molecule. DNA sequencing by synthesis is commonly achieved using one of two sensor modalities to monitor nucleotide incorporation. The two sensed modes or modalities are optical detection of fluorescently tagged nucleotides and the use of ion selective field effect transistors (ISFETs) to detect hydrogen ions that are released when a nucleotide is incorporated onto a target DNA fragment.

Some lab-on-a-chip type devices that analyze cells and their genomic content have been proposed but have all been in silicon on silicon substrates. This raises at least two major problems. One is that these silicon devices are relatively expensive and in the medical field a device of this type is almost exclusively used only once and discarded. Multiple uses require extensive cleaning which is even more costly than discarding the chip. Further in many of the tests or sensing processes, a high voltage (in excess of 50 volts) is required and silicon devices cannot withstand this voltage.

It would be highly advantageous, therefore, to remedy the foregoing and other deficiencies inherent in the prior art.

Accordingly, it is an object of the present invention to provide a new and improved metal oxide TFT-based sensor with multiple transistors and multiple sensing modalities.

It is another object of the present invention to provide a new and improved metal oxide TFT-based sensor with multiple transistors that is relatively inexpensive and easy to use.

SUMMARY OF THE INVENTION

The desired objects of the instant invention are achieved in accordance with the present invention in a metal oxide TFT-based sensor with multiple sensing modalities including an ion sensitive detector having an extended gate, a reservoir constructed to receive a sample carrying solution, and an ion sensitive electrode. The sensor further includes a photodiode, a plurality of metal-oxide thin film transistors and a signal output. A pair of the metal-oxide thin film transistors are coupled to the photodiode, the ion sensitive detector and the output so as to provide output signals at the output alternately representative of ion emissions sensed by the ion sensitive detector and fluorescence events sensed by the photodiode.

The desired objects of the instant invention are further achieved in a metal oxide TFT-based sensor with multiple sensing modalities including an ion sensitive detector positioned adjacent DNA nucleotide incorporation structure designed to have DNA target fragments or sequencing primers bonded to a surface in or on the structure for the incorporation of DNA nucleotides onto the DNA target fragments or sequencing primers, at least some of the DNA nucleotides having a fluorescent label. An illumination device is positioned in proximity to the DNA nucleotide incorporation structure to illuminate DNA nucleotides incorporated onto the DNA target fragments or sequencing primers, and the illumination device exciting the fluorescent labels when incorporation occurs. The ion sensitive detector further includes a metal oxide thin film transistor with an ion sensitive gate electrode electrically coupled to receive an electrical signal indicative of ion emissions produced by the DNA nucleotide incorporated onto DNA target fragments or sequencing primers. A photodiode is positioned adjacent the DNA nucleotide incorporation structure to sense the excited fluorescent labels. A plurality of metal-oxide thin film transistors and a signal output are included in the sensor. A pair of metal-oxide thin film transistors of the plurality of metal-oxide thin film transistors are coupled to the photodiode, the ion sensitive detector and the output so as to provide output signals at the output alternately representative of ion emissions sensed by the ion sensitive detector and fluorescence events sensed by the photodiode.

The desired objects of the instant invention are further achieved in a metal oxide TFT-based sensor with multiple sensing modalities. The sensor includes an ion sensitive detector having an extended gate, a reservoir constructed to receive a sample carrying solution, and an ion sensitive electrode. The ion sensitive detector includes DNA nucleotide incorporation structure designed to have DNA target fragments or sequencing primers bonded to a surface in or on the structure for the incorporation of DNA nucleotides onto the DNA target fragments or sequencing primers, at least some of the DNA nucleotides having a fluorescent label. An illumination device is positioned in proximity to the DNA nucleotide incorporation structure to illuminate DNA nucleotides incorporated onto the DNA target fragments or sequencing primers, the illumination device exciting the fluorescent labels when incorporation occurs. The ion sensitive detector includes a metal oxide thin film transistor with an ion sensitive gate electrode forming the extended gate and electrically coupled to receive an electrical signal indicative of ion emissions produced by the DNA nucleotide incorporated onto DNA target fragments or sequencing primers. The ion sensitive gate electrode is formed of ITO to enable dielectrophoresis (DEP) applications and allow optical transmission to an underlying photodetector. An amorphous silicon photodiode is positioned adjacent the DNA nucleotide incorporation structure to sense the excited fluorescent labels. A plurality of metal-oxide thin film transistors and a signal output are included in the sensor. A pair of metal-oxide thin film transistors of the plurality of metal-oxide thin film transistors are coupled to the photodiode, the ion sensitive detector and the output so as to provide output signals at the output alternately representative of ion emissions sensed by the ion sensitive detector and fluorescence events sensed by the photodiode.

The desired objects of the instant invention are yet further achieved in a metal oxide TFT-based sensor with multiple sensing modalities. The sensor includes an ion sensitive detector having an extended gate, a reservoir constructed to receive a sample carrying solution, and an ion sensitive electrode. The sample carrying solution further comprises target cells and may include blood, plasma, serum, or the like as well as a buffer solution. The ion sensitive detector includes a metal oxide thin film transistor with an ion sensitive gate electrode forming the extended gate and electrically coupled to receive an electrical signal indicative of cells that have settled onto the ion sensitive gate electrode. An amorphous silicon photodiode is positioned adjacent to the electrode so as to sense optical absorption of the target cells or fluorescence from fluorescent labels attached to the target cells. A plurality of metal-oxide thin film transistors and a signal output are included in the sensor. A pair of metal-oxide thin film transistors of the plurality of metal-oxide thin film transistors are coupled to the photodiode, the ion sensitive detector and the output so as to provide output signals at the output alternately representative of ion emissions sensed by the ion sensitive detector and fluorescence events sensed by the photodiode.

BRIEF DESCRIPTION OF THE DRAWINGS

The foregoing and further and more specific objects and advantages of the instant invention will become readily apparent to those skilled in the art from the following detailed description of a preferred embodiment thereof taken in conjunction with the drawings, in which.

DETAILED DESCRIPTION OF THE DRAWINGS

It should be specifically understood that metal-oxide thin film transistors (MOTFTs) have a number of key characteristics that make them especially adaptable to one-chip multimodal sensors of the present type. One key characteristic that makes MOTFTs highly useful in the present sensors is the very low (fA) source-drain leakage current and the very high ON-OFF current ratio. Another key characteristic is the high mobility (10-50) that enables low ON-resistance and the ability to source sufficient current for dielectrophoresis (DEP). That is, the low ON-resistance reduces RC time constants and enables (AC) DEP at optimal operating frequencies. Yet another key characteristic of MOTFTs is the ability to handle high voltages (>60V) which in turn enables efficient DEP. Still another key characteristic is the dual gate operation that can increase charge sensitivity by 10 to 20 times. Another key characteristic of MOTFTs is the ability to fabricate amorphous silicon (a-Si) photodiodes on top of MOTFT backplanes. All of these key characteristics and others make MOTFTs unique for use in one-chip multimodal sensors in accordance with the present invention.

Figure 1:
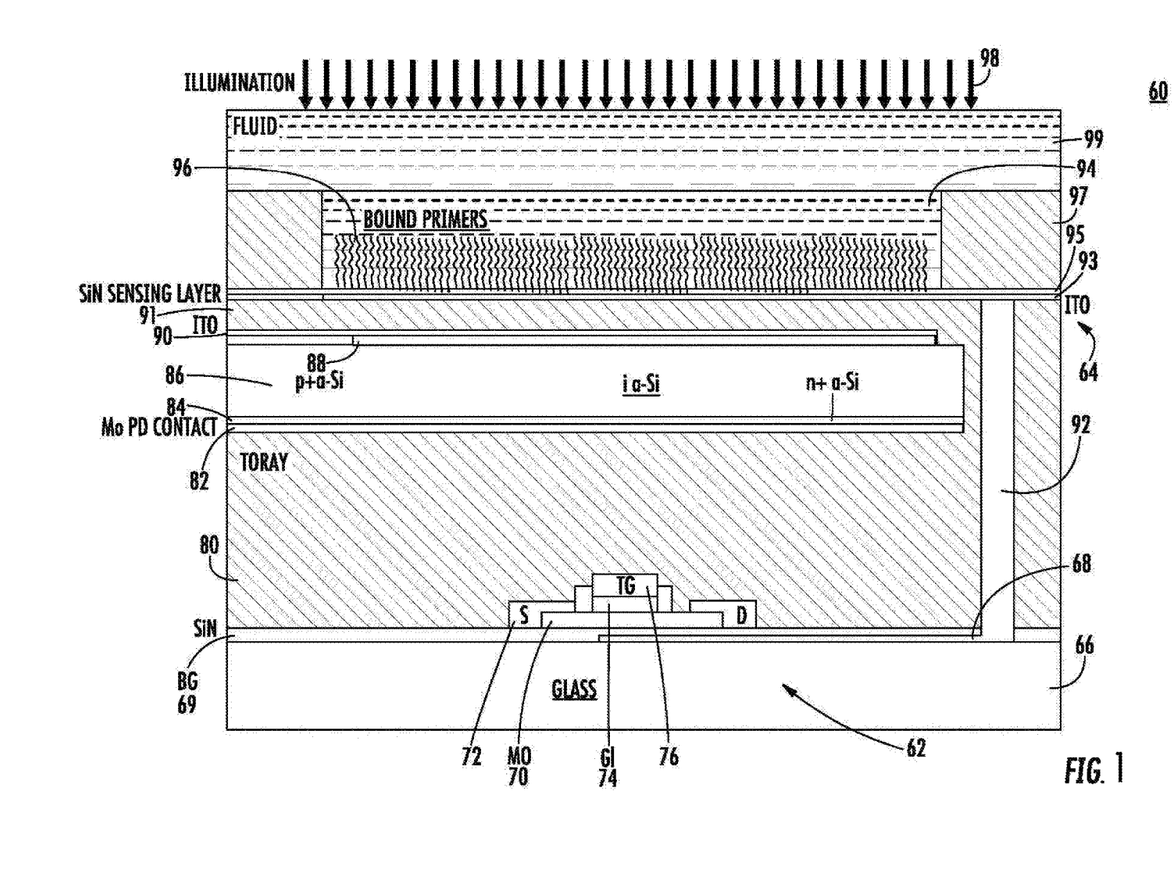
FIG. 1 is a simplified layer diagram illustrating a combined MOTFT ion sensitive and optical detection structure with an a-Si photodiode on top of an ion sensitive MOTFT.

Turning to FIG. 1, an example of a combined MOTFT ion sensitive and optical detection structure 60 is illustrated which includes and combines at least one ion sensitive MOTFT (metal oxide thin film transistor) 62 and an optical detection thin film photodiode 64. Structure 60 is fabricated on a substrate 66 which in this preferred embodiment is glass but could be other materials not necessarily transparent (unless required by the fabrication of MOTFT 62). Gate metal 68 is deposited on the surface of substrate 66 so as to extend from a central portion of structure 60, where it serves as a bottom gate for MOTFT 62, to adjacent the right-hand edge of substrate 66. A layer 69 of gate dielectric, which in this preferred embodiment is SiN but may be other insulating material, is deposited over gate metal 68. An active layer 70 of semiconductive metal oxide is deposited in overlying relationship to a bottom gate portion of gate metal 68. Source/drain contacts 72 are formed in spaced apart relationship in contact with the upper surface of active layer 70. A layer 74 of gate dielectric or insulating material is deposited on the upper surface of active layer 70 between source/drain contacts 72 and gate metal is deposited on the upper surface of gate dielectric layer 74 to define a channel in active layer 70. As will be understood, source/drain contacts 72 and top gate 76 include electrical connections (not shown) designed to electrically couple MOTFT 62 into external circuitry, such as a matrix or the like.

A thick layer 80 of insulating encapsulation material is deposited over MOTFT 62. As will be understood by artisans in the field, the insulating encapsulation material is selected to have a minimum and preferably no effect on both the electrical and chemical components of structure 60 and the subject tests. A contact layer 82 of metal is deposited on the upper surface of encapsulation layer 80 so as to extend a short distance from the right-hand edge of structure 60 to the left-hand edge where it is exposed to provide easy access as a contact terminal. A layer 84 of n+ doped a-Si is deposited over the upper surface of contact layer 82. An intrinsic or insulating layer 86 of a-Si is deposited on the upper surface of layer 84 and a layer 88 of p+ doped a-Si is deposited over a central portion of intrinsic or insulating layer 86 to form amorphous silicon photodiode 64 directly overlying MOTFT 62. An upper contact layer 90 of transparent conductive material, such as ITO or the like, is deposited over p+a-Si layer 88 and serves as an upper contact for amorphous silicon photodiode 64. In this specific embodiment, contact layer 90 extends to the left-hand edge of structure 60 where it is exposed to provide easy access as a contact terminal.

In this specific example, a substrate for target DNA fragments is formed in overlying relationship to amorphous silicon photodiode 64 as follows. A layer 91 of transparent insulating material is deposited over contact layer 90 across the entire upper surface of structure 60. A through-hole or via 92 is formed from the upper surface of layer 91 to the upper surface of gate metal 68 and is filled with metal so that an electrical contact with the bottom gate of MOTFT 62 is formed in the upper surface of layer 91. A layer 93 of transparent conductive material (e.g. indium/tin/oxide (ITO) or the like) is deposited over the upper surface of layer 91 so as to extend above the area encompassed by p+a-Si layer 88. Layer 93 also extends into contact with the metal in via 91 so as to be in electrical contact with the bottom gate of MOTFT 62 and further extends to the outer edge of structure 60 where it is exposed to provide easy access as a contact terminal. A sensing layer 95 of some transparent non-conductive material, such as SiN, tantalum oxide, or the like is deposited over the upper surface of conductive layer 93 and forms a substrate for target DNA fragments 96. A wall 97 is formed on the upper surface of sensing layer 95 so as to encircle the substrate and form a reservoir 94 to contain a liquid 99 containing DNA nucleotides on the upper surface of the substrate. An illumination source is provided above the substrate/sensing layer 95 and reservoir 94. All of the material between reservoir 94 and photodiode 64 is generally referred to as the 'bottom' of reservoir 94 for convenience.

In the operation of structure 60, a labeled nucleotide is carried by liquid 99 into enclosure 96 in proximity to the target DNA fragments on substrate/sensing layer 95, a fluorescence event will or will not occur when the target DNA fragments are illuminated by illumination source 98, depending on whether the labeled nucleotide is incorporated onto the target DNA strand by the polymerase enzyme. The presence or absence of fluorescence is sensed by photodiode 64 which appears as a signal between contacts 82 and 90 at the left edge of structure 60. Simultaneously, the incorporation of nucleotides onto the target fragments release hydrogen ions and produce a change in the pH of liquid 99 in enclosure 96. The change in pH is sensed by a small change in voltage on conductive layer 93 and, consequently, the bottom gate of MOTFT 62. The small change in voltage on the bottom gate acts similar to a bias so that a larger signal on the top gate is required to activate (i.e. turn ON or turn OFF) MOTFT 62. Thus, the small signal is essentially amplified which, depending upon the design and construction of MOTFT 62, can be as much as a factor of 10-100.

In an alternative mode of operation of structure 60, a target cell is carried by liquid 99 into enclosure 96 in proximity to the substrate/sensing layer 95. The presence of a target cell is sensed as a small change in voltage on conductive layer 93 and, consequently, the bottom gate of MOTFT 62. Charge amplified signal is then detected from the top gate of MOTFT 62.

Several examples of multi-transistor dual detection chips for use with structure 60 or similar structures are described below. Each of the below described chips has some advantages and, in some cases, may be used for additional functions (i.e. multiple sensing modalities).

Figure 2A:
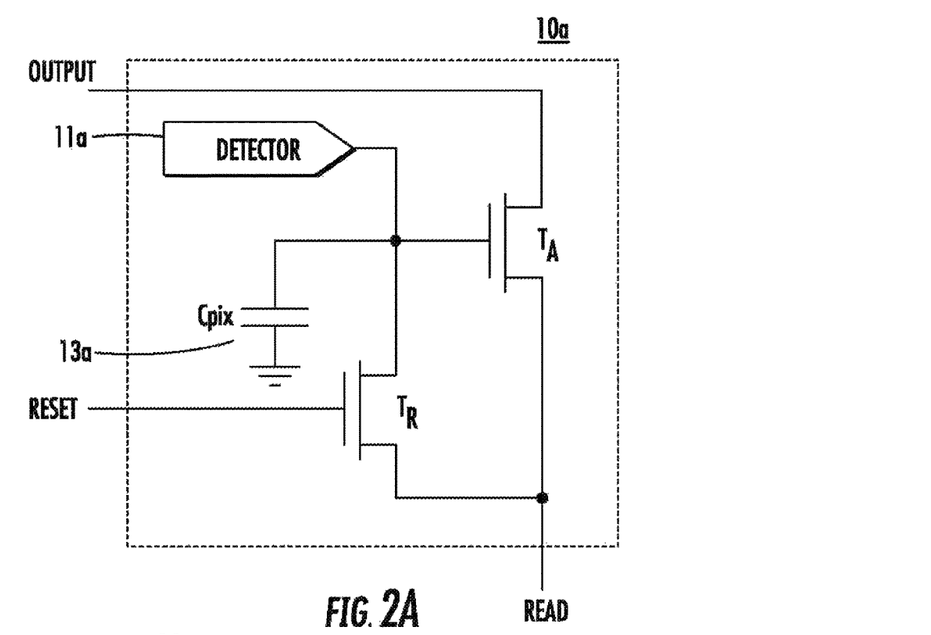
FIG. 2A illustrates a two-transistor dual detection chip with single detector and storage capacitor.

Turning to FIG. 2A a two-transistor dual detection chip 10a with single detector 11a and storage capacitor 13a is illustrated. In the operation of chip 10a, detector 11a charges capacitor 13a until the charge is sufficient to turn ON transistor TA when a READ signal is applied. An output signal indicative of the detector signal is then available at the output. Applying a reset signal discharges capacitor 13a and the next or a second detect signal can be available.

Figure 2B:
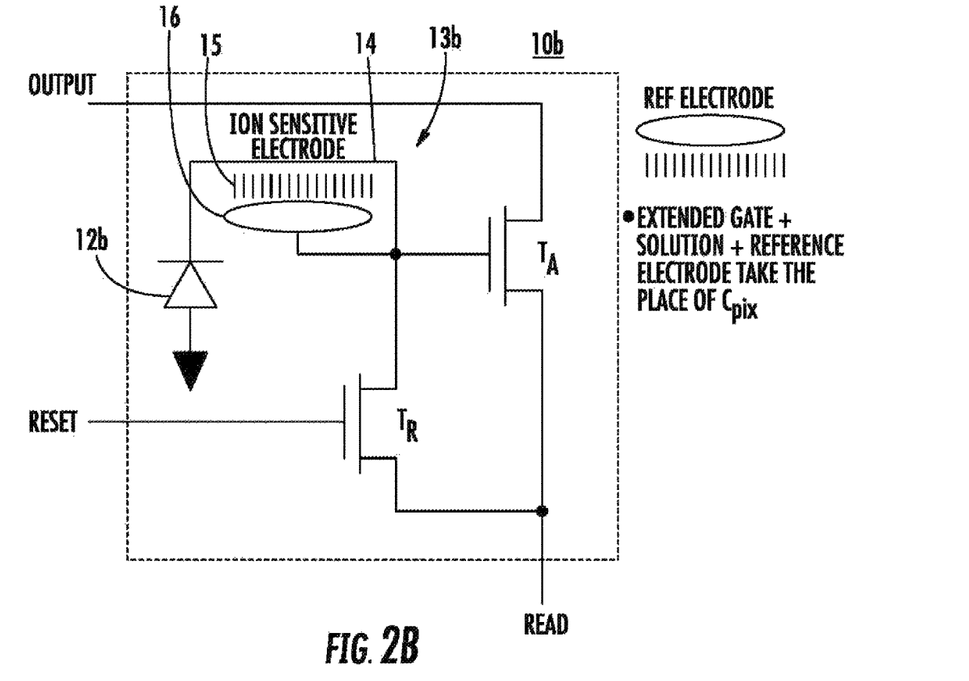
FIG. 2B illustrates a photodetector and ion sensor in a dual detection sequencing chip in accordance with the present invention.

FIG. 2B illustrates a photodetector or photodiode 12b and ion sensor 13b in a dual detection sequencing chip 10b, in accordance with the present invention. Here it should be noted that because of the use of metal-oxide TFTs, photodiode 12b can be a very simple a-Si diode. One specific example of photodetector 12b and ion sensor 13b is illustrated in FIG. 1 and described in detail above. In the operation of dual detection sequencing chip 10b, an extended gate 14, a reservoir constructed to receive a sample carrying solution 15 and an ion sensitive layer 16 form an ion sensitive detector (ion sensor 13b) as is well known in the art, and operate as a capacitor similar to storage capacitor 13a in FIG. 2A. Thus, when photodiode 12b senses an optical signal, e.g. the optical detection of fluorescently tagged nucleotides, a signal is supplied to ion sensor 13b and when sufficient charge accumulates is applied to the gate of transistor TA and a read signal provides an output signal. A reset signal will discharge ion sensor 13b or reset photodiode 12b to a reference potential and when ion sensor 13b senses a change in the pH of liquid 15 due to the release of hydrogen ions through the incorporation of nucleotides onto target fragments, a second signal will be applied to the gate of transistor TA and another read signal provides a second output signal. It should be understood that ion and optical sensing can be performed in any desired order throughout all of the dual detection chips described herein. Typically, however, the ion flow is controlled by flow and would be read first, followed by an optical read which is facilitated by turning on the light source. Thus, a two-transistor dual detection sequencing chip in accordance with the present invention is illustrated.

Figure 3:
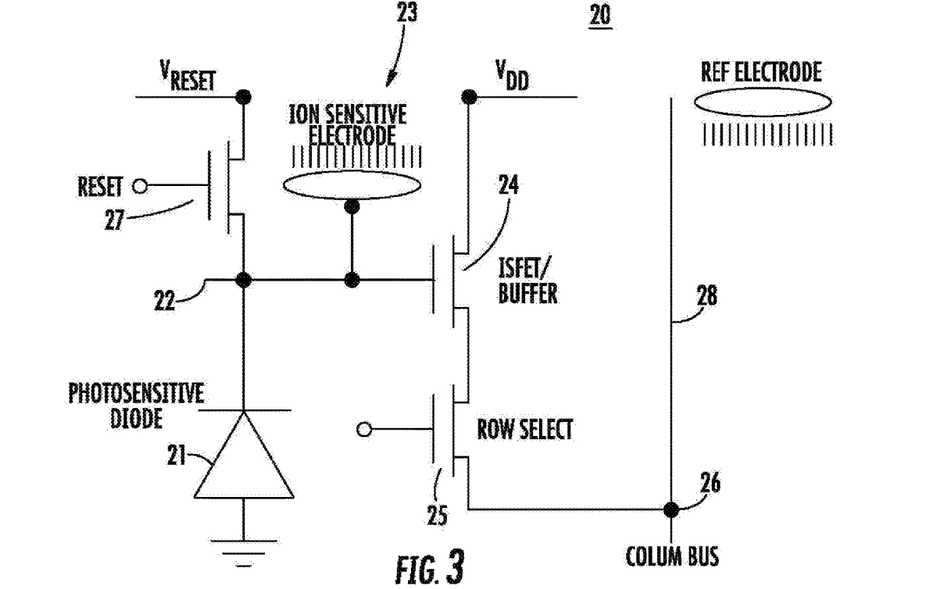
FIG. 3 illustrates a three-transistor dual detection sequencing chip in accordance with the present invention.

Turning to FIG. 3, a three transistor dual detection sequencing chip 20 in accordance with the present invention is illustrated. Three transistor chip 20 is more sensitive than the above described two transistor chip 10b and provides better separation of signals. Chip 20 includes a photodiode 21 connected between ground or a reference and a junction 22. An ion sensor 23, similar to ion sensor 13b described above, is connected to junction 22 and to the gate of a buffer transistor 24. As will be understood by those skilled in the art, chip 20 represents a pixel in an array of pixels that may be any convenient size (i.e. a plurality of pixels arranged in rows and columns). To this end, a row select transistor 25 has source/drain terminals connected in series with the source/drain terminals of buffer transistor 24. The series connected source/drain terminals are further in series between a voltage source $V_{DD}$ and a junction 26 with a column bus 28. Thus a read signal on the gate of row select transistor 25 allows a signal from the gate of buffer transistor 24 to be applied to the column bus 28. That is a read signal on the gate of row select transistor 25 and the output selection of column bus 28 specifically addresses chip 20 in the array of pixels.

In operation, when photodiode 21 senses an optical signal, e.g. the optical detection of fluorescently tagged nucleotides, a signal is supplied to ion sensor 23 and when sufficient charge accumulates is applied to the gate of buffer transistor 24. A read signal on the gate of row select transistor 25 provides an output signal on column 28. A reset transistor 27 is connected between junction 22 and a reset voltage source. A reset signal will discharge ion sensor 23 after reading the optical detection of fluorescently tagged nucleotides and when ions are sensed by ion sensor 23, a second signal will be applied to the gate of transistor 24 and another read signal provides a second output signal on column bus 28. Thus, a two-transistor dual detection sequencing chip in accordance with the present invention is illustrated.

Figure 4:
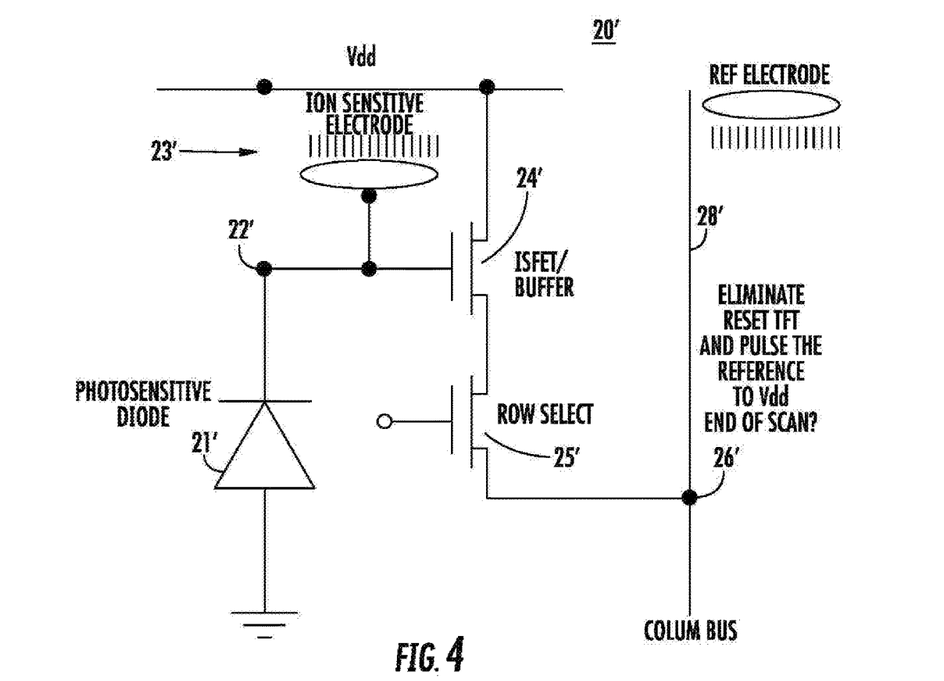
FIG. 4 illustrates a two-transistor dual detection sequencing chip with reset eliminated.

Turning to FIG. 4, a modified version of chip 20 in FIG. 3 is illustrated in which components similar to those in FIG. 3 have a similar number with a prime (') added to denote a modified version. In the modification of chip 20', reset transistor 27 is eliminated along with the reset signal input. In the operation of chip 20', the Vdd supplied to the reference electrode is pulsed at the end of each scan, applying a reset to junction 22' across the sample solution which allows any signals on junction 22' to simply dissipate.

Figure 5:
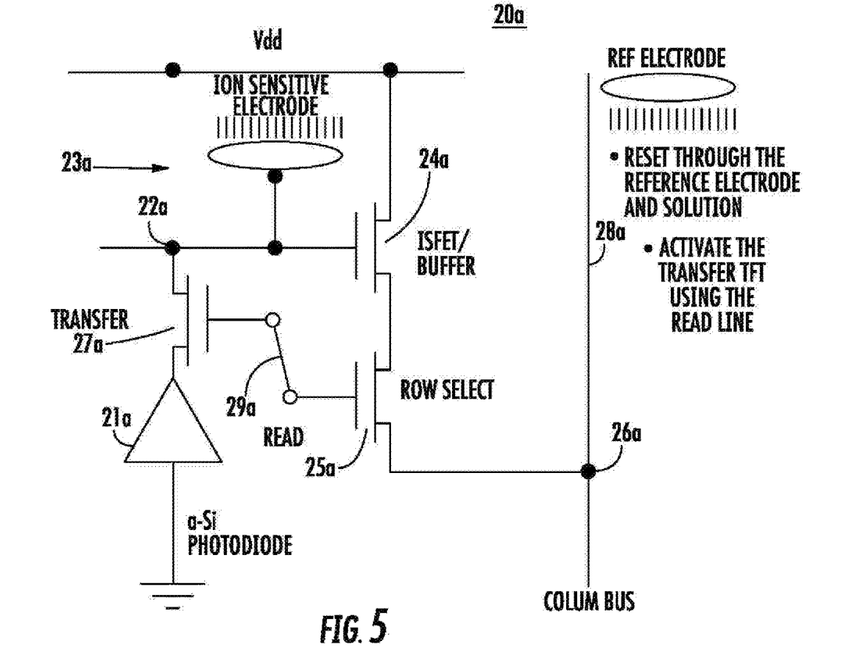
FIG. 5 illustrates a three-transistor dual detection sequencing chip with alternate reset.

Turning to FIG. 5, a slightly modified three transistor chip 20a is illustrated in which components similar to those in FIG. 3 have a similar number with an 'a' added to denote a modified version. In the modification of chip 20a, a transfer transistor 27a is connected between photodiode 21a and junction 22a. Also a switch 29a connects the read signal applied to the gate of row select transistor 25a to the gate of transfer transistor 27a when a reset is required. Thus, it is not required to generate a separate reset signal since the read signal serves that purpose.

Figure 6:
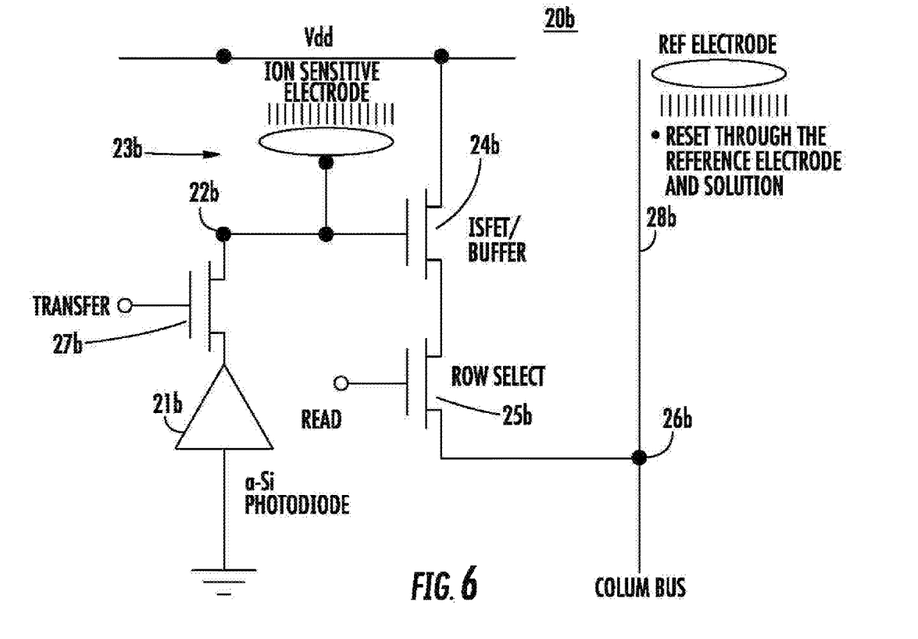
FIG. 6 illustrates an alternate embodiment of a three-transistor dual detection sequencing chip with the reset eliminated.

Turning to FIG. 6, a preferred embodiment of a three transistor chip 20b is illustrated in which components similar to those in FIG. 3 have a similar number with a 'b' added to denote a modified version. In the modification of chip 20b, a transfer transistor 27b is connected between photodiode 21b and junction 22b. The gate of transfer transistor 27b is simply connected to receive any convenient transfer signal that will connect the output of photodiode 21b to junction 22b for readout. This prevents leakage of the photodiode current out the ion sensitive electrode 23b which could reduce the optical sensitivity. Reset of the photodetector is achieved by pulsing the reset voltage onto the reference electrode.

Figure 7:
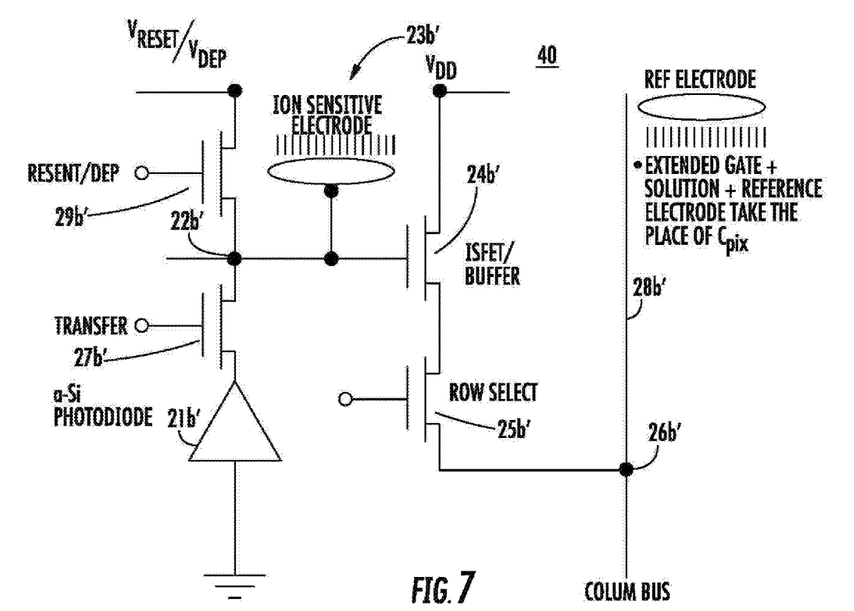
FIG. 7 illustrates a four-transistor dual detection sequencing chip in accordance with the present invention.

Referring to FIG. 7, a four-transistor dual detection sequencing chip 40 in accordance with the present invention is illustrated. Chip 40 is similar to chip 20b of FIG. 6 with all components that are the same being designated with the same numbers and a prime (') is added to indicate a modified chip. Chip 40 differs from chip 20b in that a reset/DEP transistor 29b' is connected between junction 22b' and a reset/DEP voltage source so as to apply either a reset voltage or a dielectrophoresis voltage to junction 22b'. Further, the gate of transistor 29b' is connected to receive either a reset signal or a DEP signal. Here it should be noted that in an array (i.e. chip 40 is one pixel in an array of pixels) all reset lines and all transfer lines may be connected together so that a global transfer and/or a global reset may be implemented. Further, transfer transistor 27b' and reset transistor 29b' must be activated simultaneously to reset photodiode 21b'.

As is well understood in the art, dielectrophoresis (DEP) can be used to manipulate, transport, separate, and/or sort different types of particles. Also, it is understood that all biological cells have dielectric properties making dielectrophoresis very valuable and highly useful in medical/biological fields. As understood, DEP-force is exerted on a dielectric particle when it is subjected to a non-uniform electric field. Also, fields of a particular frequency can be used to manipulate particles with great sensitivity.

Turning briefly to FIG. 1, an ion sensitive electrode (e.g. extended gate 93 in structure 60) can be provided for use in dielectrophoresis by including only indium/tin/oxide (ITO) with no additional insulating layer (e.g. layer 95 is not present). Alternatively, as the dielectrophoresis signal has a particular AC frequency, layer 95 may be included provided the capacitive impedance of the ion sensitive electrode is sufficiently low at the AC frequency. Thus, in the operation of chip 40 in FIG. 7 (in conjunction with structure 60 of FIG. 1), when a DEP signal is applied to the gate of transistor 29b' the $V_{DEP}$ voltage is applied through the source/drain directly to ITO electrode 93 and some form of dielectrophoresis can be achieved in reservoir 94. ITO electrodes have been shown in the literature to have sensitivity>50 mV/pH unit which is comparable to ion sensitive electrodes with other ion sensing layers such as silicon nitride. With an ITO electrode as described above, a reset transistor is required to prevent leakage into solution 99 in structure 60.

Figure 8:
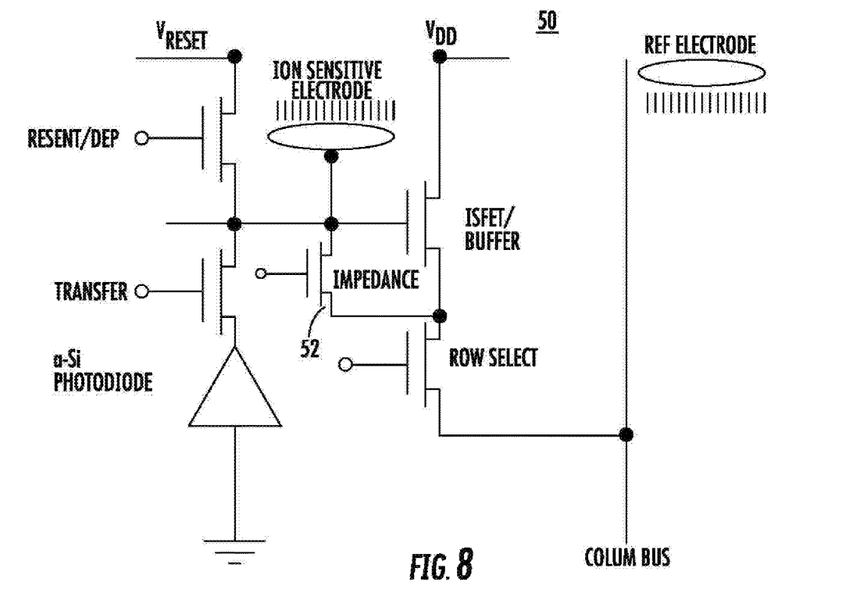
FIG. 8 illustrates a five-transistor dual detection sequencing chip in accordance with the present invention.

Referring now to FIG. 8, a five-transistor dual detection sequencing chip 50 in accordance with the present invention is illustrated. Chip 50 is similar to chip 40 of FIG. 7 with an impedance measuring transistor 52 connected between the junction (junction 22b' in FIG. 7) and the junction between the series connection of the source/drains of the buffer and row select transistors (24b' and 25b', respectively, in FIG. 7). Transistor 52 is connected to allow an impedance measurement of the ion sensitive electrode when a signal is applied to the gate thereof. Thus, circuit 50 is capable of one or more of an optical measurement, an ion sensitive charge measurement, an impedance measurement, and/or a DEP function.

Thus, new and improved metal oxide TFT-based sensors with multiple transistors and multiple sensing modalities are disclosed for a variety of different biological functions. The new and improved sensors incorporate both an optical detection process and a process of detecting hydrogen ions that are released when a nucleotide is incorporated onto a target DNA fragment, or other charged entities such as cells, DNA, or exosomes, as well as impedance measurements and DEP function capabilities. The variety of multiple transistor sensors disclosed provide a wide variety of potential tests and functions. The wide variety of tests and functions is made possible by the use of metal-oxide TFTs which include characteristics that enable the technology and all of the disclosed chips are relatively inexpensive so that use in the medical field is promoted.

Various changes and modifications to the embodiment herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. A metal oxide TFT-based sensor with multiple sensing modalities comprising:
    an ion sensitive detector including an extended gate, a reservoir constructed to receive a sample carrying solution, and an ion sensitive electrode;
    a photodiode;
    a plurality of metal-oxide thin film transistors;
    a signal output; and
    a pair of metal-oxide thin film transistors of the plurality of metal-oxide thin film transistors coupled to the photodiode, the ion sensitive detector and the output so as to provide output signals at the output alternately representative of ion emissions sensed by the ion sensitive detector and fluorescence events sensed by the photodiode.

2. The metal oxide TFT-based sensor claimed in claim 1 wherein the photodiode is an amorphous silicon diode.

3. The metal oxide TFT-based sensor claimed in claim 1 wherein the ion sensitive detector includes: DNA nucleotide incorporation structure designed to have DNA target fragments or sequencing primers bonded to a surface in or on the structure for the incorporation of DNA nucleotides onto the DNA target fragments or sequencing primers, at least some of the DNA nucleotides having a fluorescent label; the photodiode being positioned adjacent the DNA nucleotide incorporation structure; an illumination device positioned in proximity to the DNA nucleotide incorporation structure to illuminate DNA nucleotides incorporated onto the DNA target fragments or sequencing primers, the illumination device exciting the fluorescent labels when incorporation occurs and the photodiode positioned to sense the excited fluorescent labels.

4. The metal oxide TFT-based sensor claimed in claim 1 wherein the metal oxide TFT-based sensor is one pixel in an array of pixels, with the array of pixels arranged in rows and columns.

5. The metal oxide TFT-based sensor claimed in claim 4 wherein the pair of metal-oxide thin film transistors each include source/drain terminals connected in series between a voltage source and one of a column bus or row bus, one of the pair of metal-oxide thin film transistors including a gate electrode coupled to another of the column bus or row bus for receiving a read signal thereon to provide an addressing function for the one pixel.

6. The metal oxide TFT-based sensor claimed in claim 5 wherein another of the pair of metal-oxide thin film transistors includes a gate electrode coupled to the ion sensitive electrode of the ion sensitive detector and to one terminal of the photodiode.

7. The metal oxide TFT-based sensor claimed in claim 6 wherein the ion sensitive electrode of the ion sensitive detector and the one terminal of the photodiode are further coupled through a reset metal-oxide thin film transistor to a source of reset voltage, the reset metal-oxide thin film transistor having a gate electrode coupled to receive a reset signal thereon.

8. The metal oxide TFT-based sensor claimed in claim 6 wherein a transfer metal-oxide thin film transistor is connected between the one terminal of the photodiode and the gate electrode of the another of the pair of metal-oxide thin film transistors, the transfer metal-oxide thin film transistor including a gate electrode coupled to the gate electrode of the one of the pair of metal-oxide thin film transistors so as to receive the read signal thereon to provide a reset or transfer signal.

9. The metal oxide TFT-based sensor claimed in claim 6 wherein a transfer metal-oxide thin film transistor is connected between the one terminal of the photodiode and the gate electrode of the another of the pair of metal-oxide thin film transistors, the transfer metal-oxide thin film transistor including a gate electrode coupled receive a reset or transfer signal thereon.

10. The metal oxide TFT-based sensor claimed in claim 9 wherein a reset/DEP metal-oxide thin film transistor is connected between the one terminal of the photodiode and a source of reset/DEP voltage, the reset/DEP metal-oxide thin film transistor including a gate electrode coupled to receive a reset/DEP activation signal thereon.

11. The metal oxide TFT-based sensor claimed in claim 1 wherein the extended gate of the ion sensitive detector includes ITO with no additional insulating layer.

12. A metal oxide TFT-based sensor with multiple sensing modalities comprising:
an ion sensitive detector positioned adjacent DNA nucleotide incorporation structure designed to have DNA target fragments or sequencing primers bonded to a surface in or on the structure for the incorporation of DNA nucleotides onto the DNA target fragments or sequencing primers, at least some of the DNA nucleotides having a fluorescent label, an illumination device positioned in proximity to the DNA nucleotide incorporation structure to illuminate DNA nucleotides incorporated onto the DNA target fragments or sequencing primers, and the illumination device exciting the fluorescent labels when incorporation occurs, and the ion sensitive detector including a metal oxide thin film transistor with an ion sensitive gate electrode electrically coupled to receive an electrical signal indicative of ion emissions produced by the DNA nucleotide incorporated onto DNA target fragments or sequencing primers;
a photodiode positioned adjacent the DNA nucleotide incorporation structure and the photodiode positioned to sense the excited fluorescent labels;
a plurality of metal-oxide thin film transistors;
a signal output; and
a pair of metal-oxide thin film transistors of the plurality of metal-oxide thin film transistors coupled to the photodiode, the ion sensitive detector and the output so as to provide output signals at the output alternately representative of ion emissions sensed by the ion sensitive detector and fluorescence events sensed by the photodiode.

13. The metal oxide TFT-based sensor claimed in claim 12 wherein the photodiode is an amorphous silicon diode.

14. The metal oxide TFT-based sensor claimed in claim 12 wherein the metal oxide TFT-based sensor is one pixel in an array of pixels, with the array of pixels arranged in rows and columns.

15. The metal oxide TFT-based sensor claimed in claim 14 wherein the pair of metal-oxide thin film transistors each include source/drain terminals connected in series between a voltage source and one of a column bus or row bus, one of the pair of metal-oxide thin film transistors including a gate electrode coupled to another of the column bus or row bus for receiving a read signal thereon to provide an addressing function for the one pixel.

16. The metal oxide TFT-based sensor claimed in claim 15 wherein another of the pair of metal-oxide thin film transistors includes a gate electrode coupled to the ion sensitive electrode of the ion sensitive detector and to one terminal of the photodiode.

17. The metal oxide TFT-based sensor claimed in claim 16 wherein the ion sensitive electrode of the ion sensitive detector and the one terminal of the photodiode are further coupled through a reset metal-oxide thin film transistor to a source of reset voltage, the reset metal-oxide thin film transistor having a gate electrode coupled to receive a reset signal thereon.

18. The metal oxide TFT-based sensor claimed in claim 16 wherein a transfer metal-oxide thin film transistor is connected between the one terminal of the photodiode and the gate electrode of the another of the pair of metal-oxide thin film transistors, the transfer metal-oxide thin film transistor including a gate electrode coupled to the gate electrode of the one of the pair of metal-oxide thin film transistors so as to receive the read signal thereon to provide a reset or transfer signal.

19. The metal oxide TFT-based sensor claimed in claim 16 wherein a transfer metal-oxide thin film transistor is connected between the one terminal of the photodiode and the gate electrode of the another of the pair of metal-oxide thin film transistors, the transfer metal-oxide thin film transistor including a gate electrode coupled receive a reset or transfer signal thereon.

20. The metal oxide TFT-based sensor claimed in claim 19 wherein a reset/DEP metal-oxide thin film transistor is connected between the one terminal of the photodiode and a source of reset/DEP voltage, the reset/DEP metal-oxide thin film transistor including a gate electrode coupled to receive a reset/DEP activation signal thereon.

21. The metal oxide TFT-based sensor claimed in claim 20 wherein the ion sensitive gate electrode of the ion sensitive detector includes ITO with no additional insulating layer.

22. A metal oxide TFT-based sensor with multiple sensing modalities comprising:

an ion sensitive detector including an extended gate, a reservoir constructed to receive a sample carrying solution, and an ion sensitive electrode, the ion sensitive detector including DNA nucleotide incorporation structure designed to have DNA target fragments or sequencing primers bonded to a surface in or on the structure for the incorporation of DNA nucleotides onto the DNA target fragments or sequencing primers, at least some of the DNA nucleotides having a fluorescent label, an illumination device positioned in proximity to the DNA nucleotide incorporation structure to illuminate DNA nucleotides incorporated onto the DNA target fragments or sequencing primers, the illumination device exciting the fluorescent labels when incorporation occurs, and the ion sensitive detector including a metal oxide thin film transistor with an ion sensitive gate electrode forming the extended gate and electrically coupled to receive an electrical signal indicative of ion emissions produced by the DNA nucleotide incorporated onto DNA target fragments or sequencing primers, the ion sensitive gate electrode formed of ITO;

an amorphous silicon photodiode positioned adjacent the DNA nucleotide incorporation structure and the photodiode positioned to sense the excited fluorescent labels;

a plurality of metal-oxide thin film transistors;

a signal output; and a pair of metal-oxide thin film transistors of the plurality of metal-oxide thin film transistors coupled to the photodiode, the ion sensitive detector and the output so as to provide output signals at the output alternately representative of ion emissions sensed by the ion sensitive detector and fluorescence events sensed by the photodiode.

23. A metal oxide TFT-based sensor with multiple sensing modalities comprising:

an ion sensitive detector including an extended gate, a reservoir constructed to receive a sample carrying solution, and an ion sensitive electrode, the ion sensitive detector including a target cell incorporation structure designed to selectively or non-selectively bind cells to the ion selective electrode, an illumination device positioned in proximity to the target cell incorporation structure to illuminate target cells with light of specific wavelengths, and the ion sensitive detector including a metal oxide thin film transistor with an ion sensitive gate electrode forming the extended gate and electrically coupled to receive an electrical signal indicative of ion emissions produced by DNA nucleotide incorporated onto DNA target fragments or sequencing primers, the ion sensitive gate electrode formed of ITO;

an amorphous silicon photodiode positioned adjacent the DNA nucleotide incorporation structure and the photodiode positioned to sense illumination transmitted through the target cells, a plurality of metal-oxide thin film transistors;

a signal output; and a pair of metal-oxide thin film transistors of the plurality of metal-oxide thin film transistors coupled to the photodiode, the ion sensitive detector and the output so as to provide output signals at the output alternately representative of ion emissions sensed by the ion sensitive detector and optical absorption sensed by the photodiode.

24. The metal oxide TFT-based sensor claimed in claim 23 wherein the target cells are fluorescently labeled and the photodiode detects fluorescent emission from the target cells.

* * * * *